United States Patent
Kilian et al.

(10) Patent No.: US 9,597,630 B2
(45) Date of Patent: Mar. 21, 2017

(54) GAS SCRUBBER SYSTEM AND METHOD

(71) Applicant: Carollo Engineers, Inc., Costa Mesa, CA (US)

(72) Inventors: Rodolfo E. Kilian, McKinney, TX (US); Toshio Shimada, Frisco, TX (US)

(73) Assignee: Carollo Engineers, Inc., Costa Mesa, CA (US)

( * ) Notice: Subject to any disclaimer, the term of this patent is extended or adjusted under 35 U.S.C. 154(b) by 0 days.

(21) Appl. No.: 15/195,070

(22) Filed: Jun. 28, 2016

(65) Prior Publication Data

US 2016/0303504 A1    Oct. 20, 2016

Related U.S. Application Data

(62) Division of application No. 14/121,619, filed on Sep. 26, 2014, now Pat. No. 9,387,431.

(51) Int. Cl.
*B01D 53/14* (2006.01)
*B01D 53/18* (2006.01)
(Continued)

(52) U.S. Cl.
CPC ......... *B01D 53/1418* (2013.01); *B01D 53/14* (2013.01); *B01D 53/18* (2013.01); *C12M 47/18* (2013.01); *B01D 47/10* (2013.01); *B01D 53/1462* (2013.01); *B01D 53/1475* (2013.01); *B01D 2252/103* (2013.01);
(Continued)

(58) Field of Classification Search
None
See application file for complete search history.

(56) References Cited

U.S. PATENT DOCUMENTS 4,997,464 A * 3/1991 Kopf ............... B01D 19/0063
                                                96/157
5,674,312 A * 10/1997 Mazzei ................. C02F 1/20
                                                210/512.1
(Continued)

FOREIGN PATENT DOCUMENTS

WO    2014053030 A1    4/2014

OTHER PUBLICATIONS

Kilian et al. "A Sweeter Thing Was Never Found: When Life Gives You Rotten Eggs, Make Biomethane."; Research Solutions Magazine; Aug. 1, 2012; pp. 3.

*Primary Examiner* — Duane Smith
*Assistant Examiner* — Phillip Shao
(74) *Attorney, Agent, or Firm* — The Webb Law Firm

(57) ABSTRACT

A system for treating a biogas stream is described. The system includes a venturi device in communication with a biogas stream source and an influent water source to combine the biogas stream and the influent water to produce a gas-water effluent. The system also includes a degas separator in communication with the venturi device for receipt of the gas-water effluent to produce a relatively low solubility gas effluent and a relatively high solubility gas-water mixture effluent. In addition, the system includes a gas-water pressure release valve in communication with the degas separator to control release of the relatively low solubility gas effluent and a discharge pressure control valve in communication with the degas separator to control release of the relatively high solubility gas-water mixture effluent.

6 Claims, 2 Drawing Sheets

(51) Int. Cl.
*C12M 1/00* (2006.01)
*B01D 47/10* (2006.01)

(52) U.S. Cl.
CPC .. *B01D 2256/245* (2013.01); *B01D 2257/304* (2013.01); *B01D 2257/504* (2013.01); *B01D 2257/55* (2013.01); *B01D 2257/7025* (2013.01); *B01D 2258/05* (2013.01)

(56) References Cited

U.S. PATENT DOCUMENTS

| | | | |
|---|---|---|---|
| 6,193,893 B1 | 2/2001 | Mazzei et al. | |
| 6,284,023 B1 * | 9/2001 | Torkildsen | B01D 53/1456 261/DIG. 54 |
| 6,291,232 B1 * | 9/2001 | Miller, III | B01D 53/14 210/605 |
| 8,500,864 B2 * | 8/2013 | Gunther | B01D 53/1425 423/228 |
| 2003/0080037 A1 | 5/2003 | Mazzei | |
| 2006/0213370 A1 * | 9/2006 | Leonard | B01D 53/14 96/243 |
| 2007/0084340 A1 * | 4/2007 | Dou | B01D 19/0057 95/8 |

* cited by examiner

GAS SCRUBBER SYSTEM AND METHOD

CROSS REFERENCE TO RELATED APPLICATION

This application is a divisional of, and claims priority to, U.S. patent application Ser. No. 14/121,619, filed on Sep. 26, 2014, now U.S. Pat. No. 9,387,431, the entire contents of which are hereby incorporated by reference.

BACKGROUND OF THE INVENTION

This invention relates to systems and methods for removing unwanted elements from a gas stream. The new system and method treats a biogas stream that may be produced at facilities such as a municipal wastewater treatment plants that have methane gas as well as other gases such as hydrogen sulfide $H_2S$, carbon dioxide $CO_2$ and other trace gases like siloxanes.

Use of gas produced in wastewater treatment facilities has long been a challenge because of the mixture of gases in the biogas produced during treatment. Of particular interest have been natural gases such as methane that can be recycled or used in cogeneration equipment or as a vehicle fuel as a cost efficiency and for reduction in greenhouse gas generation. The burning or combustion of methane that may be contaminated with other gases such as carbon dioxide and hydrogen sulfide has been increasingly regulated by air quality control regulations. In some areas even the hydrogen sulfide must be removed from biogas produced during water treatment before the gas can be flared or burned.

Current water treatment processes and methods may normally react biogas with iron in iron sponge scrubbers to clean the gas. There are various commercially available methods of iron scrubbing processes; however, they rely on adsorption and reaction of the sulfide into an iron matrix. The matrix is regenerated by oxidation of the iron to ferric oxide and oxidation of the sulfide to elemental sulfur or sulfates. Discharge of effluents is back to the head of the treatment plant.

A more efficient method is required for biogas produced in wastewater treatment in order to realize the benefit of use of combustible gas for cogeneration use in treatment facilities. The beneficial use of biogas generated in wastewater treatment depends on the cost to separate a gas such as methane from the other gases present in order to obtain a high energy gas stream similar to commercial gas.

SUMMARY OF THE INVENTION

The present invention is directed to systems and methods for removing unwanted elements from a gas stream. A biogas stream may be combined with a water stream influent in a venturi device to produce a gas-water mixture effluent. The gas-water mixture effluent is processed in a degas separator to separate and produce a relatively low solubility gas effluent and a relatively high solubility gas-water mixture effluent. The relatively high solubility gas-water mixture effluent is processed through a discharge pressure control valve based on a selected pressure to be maintained in said degas separator and then discharged or reused.

These and other features, aspects and advantages of the present invention will become better understood with reference to the following drawings, description and claims.

DETAILED DESCRIPTION

The following detailed description represents the best currently contemplated modes for carrying out the invention. The description is not to be taken in a limiting sense, but is made merely for the purpose of illustrating the general principles of the invention.

Figure 1:
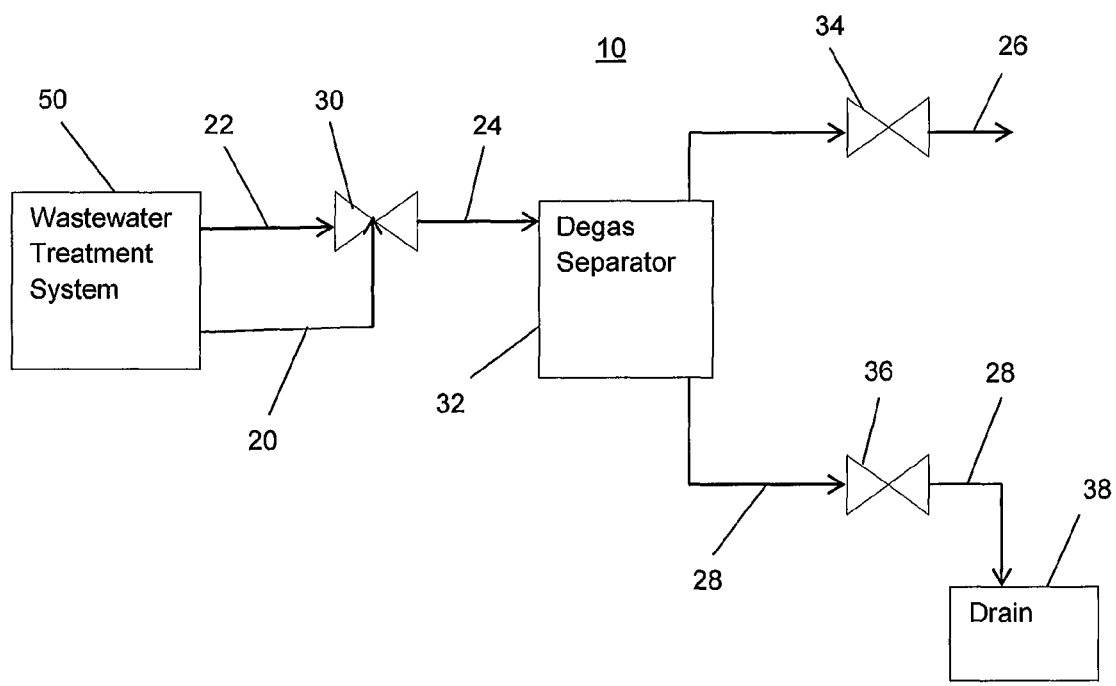
FIG. 1 illustrates a functional diagram of a gas scrubbing process according to an embodiment of the invention.

Referring to FIG. 1, a gas scrubbing process 10 receives a biogas 20 from a wastewater treatment system 50. The wastewater treatment system 50 may also serve as the source of a steady supply of water influent 22 that may be under high pressure from the treatment wash water or plant water system. This availability of water at water treatment plants is an asset that can be used to produce combustible gas such as methane gas using an efficient method as compared to existing processes.

The gas scrubbing process 10 may mix the biogas 20 in the water influent 22 in a venturi device 30. The gas-water mixture 24 produced may be communicated to a degas separator 32 to separate low solubility gas 26 such as methane gas from the gas-water mixture 24. The degas separator 32 may produce low solubility gas 26 that is controlled at a gas-water separation device 34 such as a gas pressure release valve, and may discharge a high solubility gas-water mixture 28 to be communicated to a drain 38 through a discharge pressure control valve 36.

Figure 2:
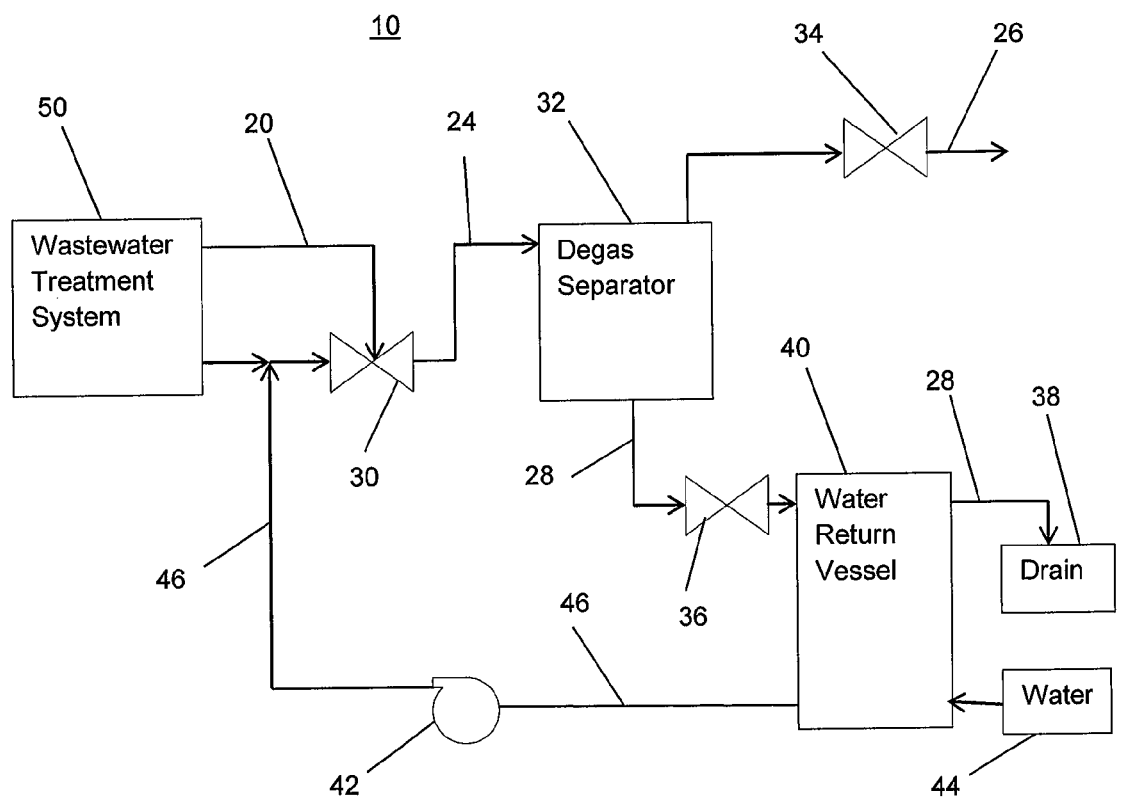
FIG. 2 illustrates a functional diagram of a gas scrubbing process with a gas-water recycle process according to an embodiment of the invention.

Referring to FIG. 2, the gas scrubbing process 10 may also include a gas-water return recycle process. The discharged high solubility gas-water mixture 28 may be communicated to a water return vessel 40. Purge overflow gas-water may be discharged to the drain 38 and the recycle high solubility gas-water mixture 46 may be returned through a pump 42 to the venturi device 30. In this gas scrubbing process 10, makeup water 44 may be introduced into the water return vessel 40 rather than supply water influent 22 being an influent directly into the venturi device 30.

The operation of the gas scrubbing system 10 separates methane gas from other gases present in gas produced from anaerobic decomposition of organic matter. The biogas 20 is introduced with pressurized water 22 in the venturi device 30 and the mixed gas-water flow is maintained in the system 10 by a pressure control valve 36 at approximately 1 to 250 psi. The biogas 20 may be urged into the venturi device 30 by the vacuum caused by the water 22 pressurized flow through the venturi device 30 or by biogas pressure flow of approximately −2 to +50 psi into the throat or constriction of the venturi device 30. The water may be pressurized to feed the venturi device 30 at pressures of approximately 10 to 500 psi. The merging of the biogas and water flow causes the relatively high soluble gases, for example, carbon dioxide, hydrogen sulfide and siloxanes, to be dissolved in the water while the methane and other relatively lower soluble gases may be maintained in gas or undissolved form. In experiments it was found the water pressure should be at least 20 psi and the system 10 operated effectively at 30 to 40 psi of water pressure. A water pressure above 250 to 500 psi caused increasing loss of methane gas to the gas-water mixture. The discharge pressure control valve 36 should be operated at as low a discharge pressure as is effective/to scrub methane gas. The valve 36 sets the operating pressure of the system 10.

The gas-water mixture 24 is communicated to a degassing separator vessel 32 for separation of the biogas lower solubility gas, for example, methane, from the gas-water mixture 24 to be conveyed to a gas-water separation device 34 that may be a pressure release valve that allows scrubbed gas to exit the system 10. The high solubility gas-water mixture 28 is conveyed to a discharge pressure control valve 36 or backpressure regulator that allows pressure release of the high solubility gas-water mixture 28 to a drain 38 or a water return vessel 40 for recycling.

The water return vessel 40 may have an overflow drain 38. A portion of the high solubility gas-water mixture 28 may be returned. The high solubility gas-water mixture 28 return rates may be between 1 and 100 percent of the water needed for operation of the venturi device 30. The water influent 22 may be between 1 and 100 percent of the water needed for venturi device 30 operation. A percentage of the two water sources may be merged to produce the total water influent for system 10 operation. There may also be make-up water 44 influent to the water return vessel 40 to maintain proper water flow and pressure conditions in the system 10.

Example

The following experimental example illustrates the use of the method and system when practicing the invention. A pilot plant size, one inch, venturi injector was connected to a degas separator and the gas effluent was controlled by a discharge pressure control valve. The high solubility gas-water mixed effluent was controlled by a discharge backpressure regulator and drained to a wastewater aeration basin. The pilot system was installed at operating wastewater treatment facilities as an alternative to flaring the acid phase gas. The following Table 1 illustrates the industry standard valves for biogas and the range and composition of the biogas tested.

TABLE 1

| Component | Typical | Observed |
|---|---|---|
| Methane (by deduction) | 55-65% | 30[1]; 50-65% |
| Carbon Dioxide | 35-45% | 68[1]; 32-39% |
| Hydrogen Sulfide | 1,500 ppm | 7,000[1]; 150-8,000 ppm |
| Water | Saturated at 95° F. | Saturated at 95° F. |
| Pressure | 2-12 in W.C.[2] | 3-7 in W.C.[2] |

Note:
[1]Acid phase gas sample:
[2]Units inches of water column

The Table 1 illustrates the differences in observed gas quality between published textbook values and the actual gas composition that was measured.

The pilot system demonstration was based on the differential solubility of the hydrogen sulfide and carbon dioxide to methane. Table 2 below illustrates the solubility differences for the three gases in water.

TABLE 2

| Compound | Solubility[1] | Difference |
|---|---|---|
| Methane | 4.11 | N/A |
| Carbon Dioxide | 300.27 | 730% |
| Hydrogen Sulfide | 256.01 | 640% |

Note:
[1]Units are ft$^3$ gas/1,000 Gallons of water.

The pressurized water source was the wastewater treatment plant wash water/plant water system as the influent to the venturi device injector inlet and the biogas was that produced at the treatment plant in an anaerobic process with the biogas influent connected to the vacuum or suction port of the venturi device. The gas-water mixture effluent of the venturi device was then processed through the degas separator for the cleaned gas, primarily methane, to be collected at the top of the degas separator at a pressure release valve, and for the high solubility gas-water mixture, primarily carbon dioxide and hydrogen sulfide in water, to be drained through a discharge pressure control valve to a drain to aeration basins of the waste treatment plant. In the experiments the pressure of the high solubility gas-water mixture 28 after the discharge pressure control valve 36 was less than 5 psi. The degas separator used was a centrifugal vortex structure that separates entrained gases from a liquid based on density differences between the gases and the liquid. Table 3 below illustrates results obtained from the pilot system testing.

TABLE 3

| Component | Inlet | Outlet |
|---|---|---|
| Methane (by deduction) | 30[1]; 50-65% | 95-98% |
| Carbon Dioxide | 68[1]; 32-39% | <2% |
| Hydrogen Sulfide | 7,000[1]; 150-8,000 | <3 ppm |
| Water | Saturated at 95° F. | Saturated at 65° F.[2] |
| Pressure | 3-7 in. W.C. | 1.5 psig |

Note:
[1]Acid phase gas sample:
[2]Water cools gas removing moisture.

Methane has limited solubility in water; therefore, a mass balance was determined to identify the amount of methane that might be lost to the water in this process. Based on the solubility of methane presented in Table 2, less than 1.8 percent of the methane in the biogas treated by the system should be lost to the water. This should make the system 98.2 percent efficient in methane recovery. A full size gas scrubbing system for a typical wastewater treatment plant that may be capable of treating 50 scfm of acid phase biogas may require a four inch venturi injector and 350 gpm of water.

While the invention has been particularly shown and described with respect to the illustrated embodiments thereof, it will be understood by those skilled in the art that the foregoing and other changes in form and details may be made therein without departing from the spirit and scope of the invention.

We claim:
1. A system for treating a biogas stream, comprising:
a biogas stream source comprising a municipal wastewater treatment facility, wherein the biogas stream comprises methane, carbon dioxide, and siloxanes and is produced from the anaerobic decomposition of organic matter;
an influent water source comprising the municipal wastewater treatment facility;
a venturi device in communication with the biogas stream source and the influent water source to combine the biogas stream and the influent water to produce a gas-water effluent;
a degas separator in communication with the venturi device for receipt of the gas-water effluent to produce a relatively low solubility gas effluent and a relatively high solubility gas-water mixture effluent;

a gas-water pressure release valve in communication with the degas separator to control release of the relatively low solubility gas effluent; and a discharge pressure control valve in communication with the degas separator to control release of the relatively high solubility gas-water mixture effluent.

2. The system of claim 1, wherein the venturi device has an injector inlet for receipt of the influent water and a constriction vacuum portion for receipt of the biogas stream.

3. The system of claim 1, wherein the degas separator is a centrifugal vortex structure that separates entrained gases from a liquid based on density differences between the gases and the liquid.

4. The system of claim 1, further comprising a water return vessel in communication with the discharge pressure control valve and the venturi device, wherein the water return vessel returns at least a portion of the relatively high solubility gas-water mixture effluent to the venturi device.

5. The system of claim 4, further comprising a pump to return the at least a portion of the relatively high solubility gas-water mixture effluent to the venturi device.

6. The system of claim 4, further comprising a makeup water source in communication with the water return vessel for providing makeup water to the water return vessel.

* * * * *